(12) United States Patent
Miller et al.

(10) Patent No.: US 6,500,233 B1
(45) Date of Patent: Dec. 31, 2002

(54) PURIFICATION OF P-XYLENE USING COMPOSITE MIXED MATRIX MEMBRANES

(75) Inventors: Stephen J. Miller, San Francisco, CA (US); Curtis L. Munson, Oakland, CA (US); Sudhir S. Kulkarni, Wilmington, DE (US); David J. Hasse, Bel Air, MD (US)

(73) Assignees: Chevron U.S.A. Inc., San Ramon, CA (US); Medal, L.P., Newport, DE (US)

( * ) Notice: Subject to any disclaimer, the term of this patent is extended or adjusted under 35 U.S.C. 154(b) by 0 days.

(21) Appl. No.: 09/697,196

(22) Filed: Oct. 26, 2000

(51) Int. Cl.[7] .......................... B01D 53/22; B01D 63/02
(52) U.S. Cl. ..................... 95/50; 96/4; 96/10; 96/14; 210/640; 502/4; 502/64
(58) Field of Search .................... 95/45, 50; 96/4, 96/7, 8, 10–14, 153, 154; 210/640; 502/4, 64, 66

(56) References Cited

U.S. PATENT DOCUMENTS

| | | | |
|---|---|---|---|
| 3,702,886 A | 11/1972 | Argauer et al. | 423/328 |
| 3,709,979 A | 1/1973 | Chu | 423/328 |
| 4,013,566 A | 3/1977 | Taylor | 96/153 X |
| 4,016,245 A | 4/1977 | Plank et al. | 423/328 |
| 4,061,724 A | 12/1977 | Grose et al. | 423/335 |
| 4,076,842 A | 2/1978 | Plank et al. | 423/328 |
| 4,080,743 A | 3/1978 | Manos | 34/9 |
| 4,080,744 A | 3/1978 | Manos | 34/9 |
| 4,120,098 A | 10/1978 | Manos | 34/9 |
| 4,127,625 A | 11/1978 | Arisaka et al. | 264/28 |
| RE29,948 E | 3/1979 | Dwyer et al. | 208/110 |
| 4,208,194 A | 6/1980 | Nelson | 96/4 |
| RE30,351 E | 7/1980 | Hoehn et al. | 55/16 |
| 4,261,832 A | 4/1981 | Schumacher et al. | 96/4 X |
| 4,342,811 A | 8/1982 | Lopatin et al. | 96/153 X |
| 4,456,527 A | 6/1984 | Buss et al. | 208/89 |
| 4,556,477 A | 12/1985 | Dwyer | 208/111 |

(List continued on next page.)

FOREIGN PATENT DOCUMENTS

| | | |
|---|---|---|
| EP | 0 219 878 | 2/1989 |
| EP | 353915 | 2/1990 |

OTHER PUBLICATIONS

Aoki, K., et al., "Separation of Gases with an A–Type Zeolite Membrane", *Ind. Eng. Chem. Res.*, 39: 2245–2251 (2000) American Chemical Society, Washington, D.C.

(List continued on next page.)

*Primary Examiner*—Robert H. Spitzer
(74) *Attorney, Agent, or Firm*—Richard J. Schulte

(57) ABSTRACT

Composite membranes capable of separating p-xylene from mixtures including p-xylene and m-xylene, and processes for purifying p-xylene using the membranes, are disclosed. The membranes are polymer membranes with a thickness of between about 10 and 1000 microns that include non-interconnected zeolite particles less than 5 microns. In one embodiment, a relatively thin polymer layer (0.5–3 microns) that includes zeolite particles is adjacent to a relatively thick polymer layer which may or may not include zeolite particles, where the thickness of the two layers is between about 10 and 1000 microns. The preferred ratio of zeolite/polymer is about 0.2 by weight. A preferred method for preparing the composite is by dispersing the zeolite in a polymer solution, casting a film of the polymer solution, and evaporating the solvent to form a polymeric film. The polymer permits passage of p-xylene and m-xylene in the vapor state, such that p-xylene diffuses at the same or a faster rate through the polymer. The polymer is preferably a polyaramide, polyimide or cellulose polymer p-Xylene and m-xylene diffuse through the zeolite, albeit at different rates. The zeolite is preferably an intermediate pore size zeolite, and more preferably, is silicalite or ZSM-5. The composite membrane is preferably in the form of a dense film or a hollow fiber. A mixture containing p-xylene and m-xylene can be enriched in p-xylene by a perstractive, pervaporative or gas-phase process through the membrane.

23 Claims, 3 Drawing Sheets

U.S. PATENT DOCUMENTS

| | | | |
|---|---|---|---|
| 4,585,747 A | 4/1986 | Valyocsik | 502/62 |
| 4,705,540 A | 11/1987 | Hayes | 55/16 |
| 4,717,393 A | 1/1988 | Hayes | 55/16 |
| 4,717,394 A | 1/1988 | Hayes | 55/16 |
| 4,761,229 A | 8/1988 | Thompson et al. | 210/321.82 |
| 4,826,667 A | 5/1989 | Zones et al. | 423/277 |
| 4,838,900 A | 6/1989 | Hayes | 55/16 |
| 4,851,505 A | 7/1989 | Hayes | 528/353 |
| 4,859,442 A | 8/1989 | Zones et al. | 423/277 |
| 4,863,496 A | 9/1989 | Ekiner et al. | 55/158 |
| 4,871,494 A | 10/1989 | Kesting et al. | 96/10 X |
| 4,880,442 A | 11/1989 | Hayes | 55/16 |
| 4,912,197 A | 3/1990 | Hayes | 528/353 |
| 4,925,459 A | 5/1990 | Rojey et al. | 95/50 |
| 4,925,545 A | 5/1990 | Murel | 204/182.9 |
| 4,925,562 A | 5/1990 | Te Hennepe et al. | 210/640 X |
| 4,935,490 A | 6/1990 | Hayes | 528/353 |
| 4,961,539 A | 10/1990 | Deem | 241/36 |
| 5,019,263 A | 5/1991 | Haag et al. | 210/640 X |
| 5,053,373 A | 10/1991 | Zones | 502/64 |
| 5,104,425 A | 4/1992 | Rao et al. | 95/50 X |
| 5,104,532 A | 4/1992 | Thompson et al. | 210/224 |
| 5,110,478 A | 5/1992 | Haag et al. | 95/50 X |
| 5,200,377 A | 4/1993 | Zones et al. | 502/62 |
| 5,202,014 A | 4/1993 | Zones et al. | 208/46 |
| 5,320,512 A | 6/1994 | Moore, Sr. | 425/131.5 |
| 5,716,527 A * | 2/1998 | Deckman et al. | 210/651 |
| 5,753,011 A | 5/1998 | Sircar et al. | 95/50 X |
| 5,755,967 A | 5/1998 | Meagher et al. | 210/640 |
| 5,763,347 A * | 6/1998 | Lai | 502/4 |
| 5,772,735 A | 6/1998 | Sehgal et al. | 96/4 X |
| 5,942,119 A * | 8/1999 | Deckman et al. | 95/50 X |
| 5,968,366 A * | 10/1999 | Deckman et al. | 95/50 X |
| 6,117,328 A * | 9/2000 | Sikdar et al. | 95/50 X |
| 6,193,784 B1 * | 2/2001 | Yazawa et al. | 96/11 X |

OTHER PUBLICATIONS

Bakker, W., et al., "Permeation characteristics of a metal-supported silicate–1 zeolite membrane", *J. Membrane Sci.*, 117: 57–78 (1996) Elsevier Science, Amsterdam.

Flanigen, E., et al., "Silicalite, A New Hydrophobic Crystalline Silica Molecular Sieve", *Nature*, 271: 512 (1978) Macmillan Journals Ltd., London.

Funke, H., et al., "Separation of Hydrocarbon Isomer Vapors with Silicalite Zeolite Membranes", *Ind. Eng. Chem. Res.*, 35: 1575–1582 (1996) American Chemical Society, Washington, D.C.

Kokotailo, G., et al., "Structure of synthetic zeolite ZSM–5", *Nature*, 272: 437–438 (1978) Macmillan Journals, Ltd., London.

Keizer, K., et al., "Two component permeation through thin zeolite MFI membranes", *J. Membrane Sci.*, 147: 159–172 (1998) Elsevier Science, Amsterdam.

"New Japanese Processes Promise Cheaper Styrene & Xylenes," *Petroleum & Petro–chemical International*, Dec. 1972, vol. 12, No. 12., pp. 64–68.

Olson, D., et al., "Crystal Structure and Structure–Related Properties of ZSM–5", *J. Phys. Chem.*, 85: 2238 (1981) American Chemical Society, Washington, D.C.

van de Graaf, J., et al., "Methodological and operational aspects of permeation measurements of silicalite–1 membranes", *J. Membrane Sci.*, 144: 87–104 (1998) Elsevier Science, Amsterdam.

Xomeritakis, G. and Tsapatsis, M., "Permeation of Aromatic Isomer Vapors through Oriented MFI–Type Membranes Made by Secondary Growth", *Chem. Mater.*, 11: 875 (1999) American Chemical Society, Washington, D.C.

\* cited by examiner

US 6,500,233 B1

PURIFICATION OF P-XYLENE USING COMPOSITE MIXED MATRIX MEMBRANES

FIELD OF THE INVENTION

The present invention relates to separation membranes with the ability to separate p-xylene from mixtures including p-xylene, m-xylene, o-xylene and ethylbenzene.

BACKGROUND OF THE INVENTION

Para-xylene is a chemical intermediate used in the manufacture of resins, pharmaceuticals, and phthalic acid. It is commonly produced by a reforming reaction, along with ethylbenzene and the other xylene isomers, ortho-xylene and meta-xylene. Para-xylene is typically about thirty mole percent of the product composition.

The recovery of purified p-xylene from this mixture is a difficult and expensive process. Crystallization is the most common industrial method for recovering para-xylene. A limitation of this method is that it is relatively energy and capital intensive. Another method involves simulated-moving-bed (SMB) adsorption followed by crystallization. This method is also relatively expensive, especially since the SMB bed must adsorb a large fraction of the total feed.

Pervaporation, perstraction and gas separation methods have been developed for separating various product mixtures. Mixtures to be separated are contacted as liquids (pervaporation) or vapors (vapor permeation) with one side (the feed side) of a pore-free membrane. Suitable membranes show a high permeation capability (permeability) for at least one component of the mixture, whereas other components will not pass or only pass to a limited extent. The driving force for the transport across the membrane is the gradient of the partial pressure of each permeating component between the feed side and the permeate side of the membrane. At the permeate side one obtains under reduced partial pressure a material stream having a composition different from that of the mixture at the feed side to be separated. The methods of pervaporation and vapor permeation can thus advantageously be used to separate mixtures that are otherwise difficult to separate (such as azeotropic mixtures or components having similar boiling points).

These methods generally employ membranes in the form of sheets, tubes, hollow fibers, and in spiral wound configuration. Hollow fiber, asymmetric membranes are particularly attractive in that the fiber provides high surface area per volume and the asymmetric mode allows for less mass transfer resistance as compared to similar homogeneous materials.

U.S. Pat. No. 4,925,459 discloses a mixed matrix polymer membrane incorporating a zeolite (ZSM-5) and the use of the membrane to separate p-xylene from mixtures of p-xylene and m-xylene. The ratio by weight of polymer to zeolite is greater than 1. A limitation of this approach is that, when the membrane includes a polymer/zeolite ratio this high, the membrane tends to be brittle.

It would be desirable to provide additional devices and processes for isolating para-xylene from a mixture of xylenes and, optionally, ethylbenzene, particularly using membrane technology. The present invention provides such processes.

SUMMARY OF THE INVENTION

In its broadest aspect, the present invention is directed to a mixed matrix composite (MMC) membrane capable of separating p-xylene from ethylbenzene and other xylene isomers, and a process for purifying p-xylene using the membrane.

The composite membrane includes a polymer and small, non-interconnected zeolite particles encapsulated in the polymer. The composite membrane is preferably in the form of a sheet, tube or hollow fiber.

The polymer is a polymer that permits passage of p-xylene and m-xylene such that p-xylene diffuses at the same or a faster rate through the polymer. The polymer is generally a polyaramide, polyimide or cellulose polymer.

The zeolite is a zeolite through which p-xylene and m-xylene diffuse, albeit at different rates. The composite permits p-xylene to diffuse through at a faster rate than m-xylene. The zeolite is preferably an intermediate pore size zeolite and, more preferably, is silicalite or ZSM-5. The ratio of zeolite/polymer is typically between about 0.05 and 0.4, preferably about 0.2 to 0.4, by weight. Membranes with significantly higher zeolite/polymer ratios (for example, about 0.65 or higher) tend to be brittle.

A preferred method for preparing polymeric films is by dispersing the zeolite in a polymer solution, casting a film of the polymer solution, and evaporating the solvent to form a polymeric film.

One method for preparing hollow fibers is to melt the polymer, mix in the zeolite particles, and extrude the polymer/zeolite blend through a tubular capillary nozzle with a core fluid used for the purpose of retaining the hollow fiber shape.

Another method involves extruding a polymer spin dope (or spinning solution) formulation including zeolite particles through a spinneret to provide a nascent hollow fiber. The nascent fiber is then contacted with a fluid to coagulate the fiber into a polymer membrane, thus entrapping the zeolite particles in the polymer membrane.

A mixture containing p-xylene and m-xylene can be enriched in p-xylene by a gas-phase, perstraction or pervaporation process through the composite membrane. Pervaporation provides superior selectivity.

Preferred conditions for enriching by perstraction are any combination of feed pressure and temperature where the temperature is just below the boiling point at that pressure. Permeate pressures should be below the feed pressure enough to ensure complete vaporization at the operating temperature. Preferable ranges are temperatures between 30 and 150 degrees Centigrade and feed pressures of 14 psia and 35 psia. Permeate pressures have a preferred range of 0 to 10 inches of vacuum gauge.

In addition to purifying p-xylene and m-xylene, the membranes can be used to separate any molecules that are known to be separated using zeolites, by selecting the appropriate zeolite to incorporate into the polymer membrane.

DETAILED DESCRIPTION OF THE INVENTION

Figure 1:
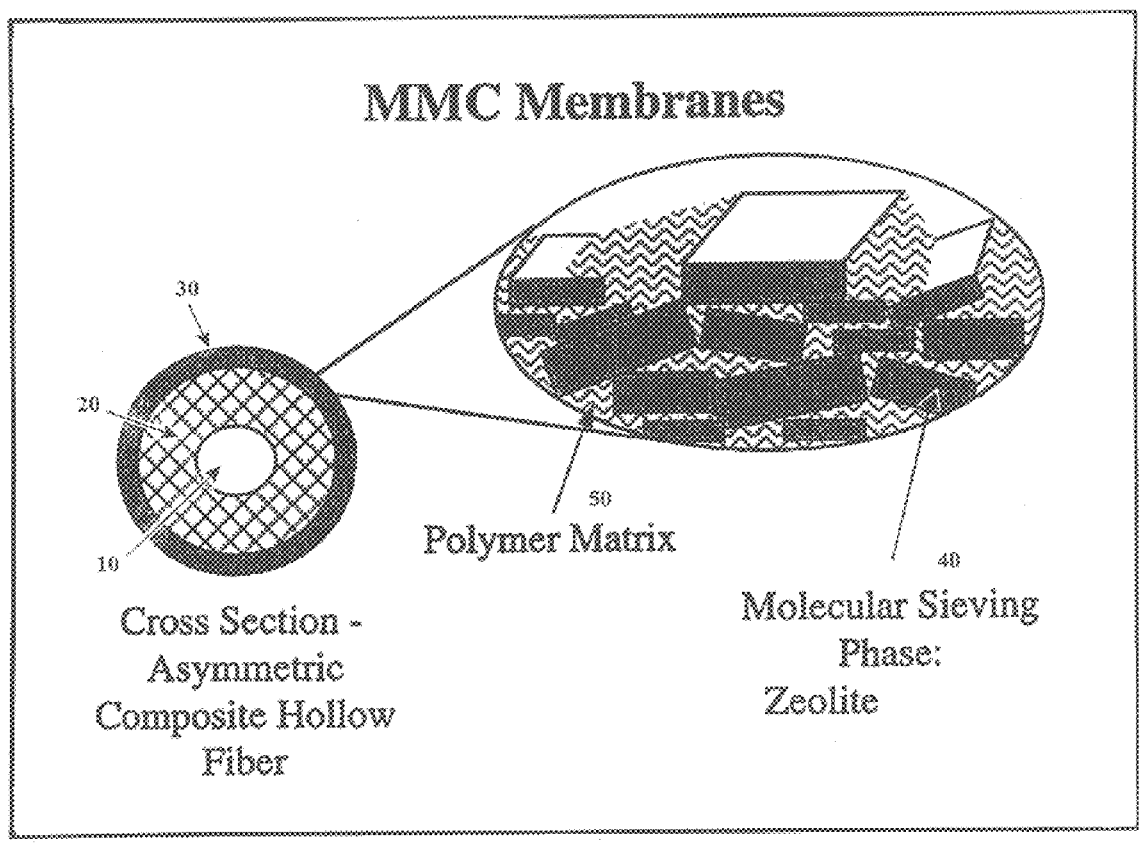
FIG. 1 is a cross section of an example of the asymmetric composite hollow fiber membranes described herein.

The present invention is directed to composite membranes and the use of the membranes to isolate para-xylene (also known as p-xylene or pX) from a mixture which includes ethyl benzene and a mixture of xylenes, and in particular from meta-xylene (also known as m-xylene or mX). The composite permits p-xylene to diffuse through at a faster rate than m-xylene.

The membranes are suitable for enriching the proportion of p-xylene in a product mixture including p-xylene and m-xylene. Such product mixtures are routinely found in the catalytic reforming of $C_{6-8}$ feedstocks, for example via the AROMAX® Process or platforming or rheniforming processes. These processes are well known to those of skill in the art, and are described, for example, in *Petroleum & Petrochemical International*, Volume 12, No. 12, pages 65 to 68, as well as U.S. Pat. No. 4,456,527 to Buss et al., the contents of which are hereby incorporated by reference. The membranes can also be used, for example, to recover ethylbenzene from recycle streams, or to separate other isomers; for example 2,6-dimethylnaphthalenes from mixtures of alkylnaphthalenes.

The composite membrane includes a polymer and non-interconnected zeolite particles encapsulated in the polymer. The composite membrane has more strength than the polymer itself. The resulting composite has a steady state permeability that differs from the steady state permeability possessed by the polymer.

Polymer Selection

The polymer is a polymer that permits passage of p-xylene and m-xylene (or other mixtures to be separated) in the vapor state, such that p-xylene diffuses at a faster rate through the polymer. Preferably, the rate at which p-xylene passes through the polymer is at least 1.5 times faster than the rate at which m-xylene passes through the polymer.

Flexible polymers are preferred over rigid polymers. Examples of suitable polymers include cellulose polymers, polyaramides, polyamides, polyimides, polyamide/imides, polyamidehydrazides, polyhydrazides, polyimidazoles, polybenzoxazoles, polyester/amide, polyester/imide, polycarbonate/amides, polycarbonate/imides, polysulfone/amides, polysulfone imides, and the like, copolymers and blends thereof. (Additionally classes include polyvinyledene fluorides and polyacrylonitriles.) Examples of these polymers include those described in U.S. Pat. Nos. RE 30,351; 4,705,540, 4,717,393; 4,717,394; 4,912,197; 4,838,900; 4,935,490; 4,851,505; 4,880,442; 4,863,496; 4,961,539; and European Patent Application 0 219 878, all of which are incorporated by reference. Preferably, the polymers include at least one of either of cellulose polymers, polyamides, polyaramides, polyamide/imides or polyimides. Most preferably, the polymers include polyaramides.

Zeolite Selection

The zeolite is a zeolite through which p-xylene and m-xylene diffuse, albeit at different rates. Examples of zeolites suitable for use in the present invention include intermediate pore size zeolites. Intermediate pore size zeolites have pore sizes in the range of between about 5 and 7 angstroms.

Examples of useful intermediate pore size zeolites include ZSM-5, ZSM-11, ZSM-22, ZSM-23, ZSM-35, ZSM-48, ZSM-57, SUZ-4, SSZ-23, SSZ-25, cesium modified SSZ-25, SSZ-28, SSZ-32, SSZ-33, SSZ-36 and silicalite. Preferred intermediate pore size zeolites include silicalite and ZSM-5. ZSM-5 is described in U.S. Pat. No. Re. 29,948 (of original U.S. Pat. No. 3,702,886). ZSM-11 is described in U.S. Pat. No. 3,709,979. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is described in U.S. Pat. No. 4,585,747. SUZ-4 is described in EP Application No. 353,915. SSZ-23 is described in U.S. Pat. No. 4,859,442. SSZ-25 is described in U.S. Pat. Nos. 4,826,667 and 5,202,014. SSZ-28 is described in U.S. Pat. No. 5,200,377. SSZ-32 is described in U.S. Pat. No. 5,053,373. SSZ-36 is described in U.S. Serial No. 60/034,252. Silicalite is a hydrophobic crystalline silica-based molecular sieve which has been developed and patented (see U.S. Pat. No. 4,061,724 to Gross et al.). A detailed discussion of silicalite may be found in the article "Silicalite, A New Hydrophobic Crystalline Silica Molecular Sieve"; *Nature*, Vol. 271, Feb. 9, 1978, incorporated herein by reference. MFI zeolites (of which ZSM-5 and silicalite are examples) can be used. Such zeolites are described, for example, in Kokotailo et al., *Nature*, 272, 437 (1978), Olson et al., *J. Phys. Chem.*, 85, 2238 (1981), and Flanigen et al., *Nature*, 271, 512 (1978). The entire contents of all these patents and patent applications are incorporated herein by reference. Other zeolites which selectively adsorb or diffuse para-xylene over meta-xylene can also be used.

Cation modification of zeolites can be used to affect the m-xylene/p-xylene separation. Routine experimentation can be used to optimize these separations.

The particle size of the zeolites is less than 5 microns, more preferably less than 1 micron. The zeolite particle size can be reduced after synthesis such as by high shear wet milling. Prior to membrane formation, the zeolite may also be silanated, either during wet milling or separately.

It is believed that silanation permits improved bonding between the zeolite outer surface and the polymer. Suitable silane compounds include 3-aminopropyldimethylethoxysilane and 3-isocyanatopropyldimethylchlorosilane. Silanation can be carried out, for example, by mixing the zeolite in an ethanol/water mixture containing the silane compound for a period of time (a few minutes up to a few hours), then recovering the treated zeolite and washing with ethanol to remove excess silane.

Spin Dope Formulations

The polymers can be used to form spin dope formulations, which can be spun into hollow fibers. The spin dope formulations can be formed by dissolving one or more of the aforementioned polymers in a suitable solvent, and dispersing an appropriate amount of zeolite particles in the solvent. Examples of suitable solvents include organic solvents such as N-methyl-2-pyrrolidone (NMP), N-acetylmorpholine, N,N-dimethylacetamide (DMAc), N,N-dimethylformamide (DMF), dioxane, dimethylsulfoxide (DMSO), hexamethylphosphoramide, as well as inorganic solvents such as sulfuric acid. Preferably, the solvents include NMP, DMAc, DMF, and DMSO.

The spin dope formulations used to form the membranes described herein have viscosities and molecular weights that enable the dope to be extruded through a spinneret to form a hollow fiber. Generally, the viscosities and molecular weights of the dope are sufficient to enable flow of the spin dope through the spinneret, but are high enough that the polymer can retain the form of the extruded hollow fiber upon leaving the spinneret. Typical zero shear viscosities of the spin dope at 70° C. are in excess of several hundred poise, preferably in the range of 1200 to 5000 poise.

Composite Membrane

The membrane includes a polymer layer, preferably comprising a polyaramide or cellulose polymer, with encapsulated zeolite particles. The membrane has the ability to separate p-xylene from m-xylene. It is permeable to these substances, and has adequate strength, heat resistance, durability and solvent resistance to be used in commercial purifications. The thickness of the polymer layer is between about 10 and 1000 microns. The ratio of zeolite/polymer is between about 0.05 and 0.4, preferably about 0.2 to 0.4 by weight.

In some embodiments, the composite membrane is an asymmetric membrane, and includes a relatively thin layer (0.1–3 microns) of the polymer/zeolite membrane, and a relatively thick polymer layer (5–1000 microns), to provide a total membrane thickness of between about 10 and 1000 microns. Preferably, the relatively thin layer is intimately adhered to the relatively thick layer.

While not wishing to be bound to a particular theory, the zeolite is believed to improve the performance of the composite by including holes/pores with a size that permits p-xylene to pass through, but either not permitting m-xylene to pass through, or permitting it pass through at a significantly slower rate. An advantage of the composite membranes described herein over membranes including primarily the zeolites (for example, membranes including >60 wt % zeolite) is that they are significantly less brittle. It may be desirable to avoid blocking the pores of the zeolites to avoid minimizing the effectiveness of the membranes.

The diffusivity of p-xylene through a polymer/zeolite membrane can be measured using techniques well known to those of skill in the art, as described, for example, in Funke et al., *Ind. Eng. Chem. Res.*, 35:1575–1582 (1996), van der Graaf et al., *J. Membrane Sci.*, 144:87–104 (1998) and Bakker et al., *J. Membrane Sci.*, 117:57–78 (1996). Measurement of p-xylene separation in the gas phase is described, for example, in Leizer et al., *J. Membrane Sci.*, 147:159–172 (1998) and Xomeritakis et al., *Chem. Mater.*, 11:875 (1999). Gas permeability measurement generally is described, for example, in Aoki et al., *Ind. Eng. Chem. Res.*, 39:2245–2251 (2000). The contents of each of these references is hereby incorporated by reference.

The membranes can be used in any convenient form such as sheets, tubes or hollow fibers. Hollow fibers are preferred, since they provide a relatively large membrane area per unit volume. Sheets can be used to fabricate spiral wound modules or plate-frame modules familiar to those skilled in the art. Those of skill in the art can readily use such membranes, sheets, tubes and hollow fibers to perform separations.

The following preparation describes a particularly preferred embodiment of the membranes described herein:

Membranes can be prepared using ZSM-5 or silicalite as the zeolite, with preferred particle sizes of between 0.1 and 3 microns, more preferably less than one micron. The zeolite may be silanated with a monofunctional aminopropyl silane such as 3-aminopropyldiisopropylethoxysilane. The zeolite may be further sized with a polymer coating, where the polymer can be the same polymer used as the matrix polymer, or can be another polymer compatible with the matrix polymer. Polyaramides based on m-phenylene diamine and iso/terephthalic acids, polyimides such as Ultem® (m-phenylene diamine and bisphenol-A dianhydride), cellulosic esters such as cellulose acetate, and vinyl or vinylidene polymers such as poly(vinylidene fluoride) are preferred matrix polymers.

N-methyl pyrollidone, dimethyl acetamide, dimethyl sulfoxide and dimethyl formamide are preferred solvents for polyaramide, polyimide or PVDF. Dioxane and acetone are preferred solvents for cellulosic esters. Additives such as tetramethylsulfone, inorganic salts, tetrahydrofuran and ethyl acetate may be added to the solvent. The zeolite particles, whether treated or neat, are added to a small amount of the neat solvent and dispersed under high shear, for example, with ultrasonication or by mechanical means such as a rotary mixer, to form a suspension.

Conventional methods can be used to prepare a solution including the polymer, solvent and additives. This solution can be added, with mixing, to the suspension of zeolite particles to form a spin dope. The concentration of the polymer in the polymer solution is chosen so that the final polymer concentration in the spin dope, Cp (as used herein, the ratio of the weight of polymer over the total weight of the polymer, solvents and additives) is the desired value. Preferably, Cp ranges from 0.15 to 0.30, preferably 0.20 to 0.25 for flat films, and 0.25 to 0.30 for hollow fibers. The zeolite loading in the spin dope (weight zeolite /weight polymer) is between 0.10 and 0.40.

For composite fiber spinning, the polymer solution including the zeolite particles is referred to as the sheath solution. A core solution that does not include zeolite particles is prepared from a polymer such as a polyaramide, polyimide, cellulose ester or PVDF in a solvent, and optionally includes additives.

A composite fiber is spun by simultaneously co-extruding the sheath and core polymer solutions to form a nascent membrane, followed by precipitation in water to form a composite multi-component membrane. The fiber includes a dense or asymmetric gas separating layer containing both polymer and zeolite and a microporous polymeric layer which structurally supports the separating layer. A suitable spinneret assembly for the co-extrusion is described in U.S. Pat. No. 5,320,512, the contents of which are hereby incorporated by reference. The spinneret may be maintained at 60 to 100° C. A liquid stream consisting of water and solvent may be injected in the bore of the nascent hollow fiber to maintain its configuration. The nascent membrane passes through an air gap into an aqueous coagulation medium. The resultant membrane is then wound on a take-up roll or collected in a can. The coagulated membrane can be washed further to remove residual solvent and then air dried or dehydrated by solvent exchange. The hollow fibers are formed into bundles by potting the open ends of the fibers into tube sheet(s) and then fitted in a pressure vessel.

The membrane can be prepared in flat sheet form by knife coating a porous web drawn over a casting drum. The knife coating can be done by directly coating the microporous web with a sheath solution or by coating the web sequentially with the core solution and then the sheath solution. The coated web is then coagulated in an aqueous bath. The web is then further washed by passing it through wash baths and then either air dried or dehydrated by solvent exchange. The dried sheet is cut to required lengths and either formed into spiral wound modules or assembled into plate-frame stacks.

Methods of Forming Polymer Films/Sheets

The membrane can be prepared by incorporating adsorbent (zeolite) particles within the membrane material. A preferred method for preparing polymeric films/sheets incorporating the particles involves:

(a) forming a slurry of the adsorbent particles in a solvent in which the membrane material is soluble;

(b) thoroughly stirring the slurry so as to obtain a highly uniform dispersion of the particles in the solvent (and/or subjecting the slurry to ultrasound);

(c) adding the membrane material to the slurry while continuing to stir the slurry until a uniform suspension is obtained; and (d) casting the solution to obtain the composite membrane.

Another method of preparation:
(a) and (b) as above;
(c) preparing the polymer solution at a higher concentration than required finally;
(d) adding the slurry to the polymer solution while continuing to stir the solution until a uniform suspension is obtained;
(e) casting the solution to obtain the composite membrane.

Sheets can be used to fabricate a flat stack permeator comprising a multitude of membrane layers alternately separated by feed-retentate spacers and permeate spacers. The layers can be glued along their edges to define separate feed-retentate zones and permeate zones. Devices of this type are described in U.S. Pat. No. 5,104,532, the contents of which are hereby incorporated by reference.

Methods of Forming Tubes

Tubes can be formed, for example, by heating a preformed polymer, mixing in zeolite particles, and extruding the polymer/zeolite mixture. In one embodiment, a relatively thick inside layer (5–1000 microns) includes polymer but no zeolites, and a relatively thin outside layer (0.1–3 microns) includes both polymer and zeolites. Tubes can be used in the form of multi-leaf modules wherein each tube is placed in parallel with other flattened tubes. Internally, each tube contains a spacer. Adjacent pairs of flattened tubes can be separated with layers of spacer material. The flattened tubes with positioned spacer material are fitted into a pressure resistant housing equipped with fluid entrance and exit means. The ends of the tubes are clamped to create separate interior and exterior zones relative to the tubes in the housing. This type of device is described in U.S. Pat. No. 4,761,229, the contents of which are hereby incorporated by reference.

Methods of Forming Hollow Fibers

Hollow asymmetric fiber membranes that have a separating skin at either the exterior or interior surface of the fiber have a graded density skin, that is, a skin which exhibits maximum density on the exterior of the fiber at the surface which is farthest from the porous substructure. Asymmetric membranes are substantially chemically homogeneous and exhibit selective permeation for at least one gas of a gaseous mixture over that of at least one other gas of that mixture.

Melt Extrusion

Hollow fibers can be formed, for example, by extruding a molten polymer/zeolite mixture through a tubular capillary nozzle with or without a core fluid used for the purpose of retaining the hollow fiber shape, and allowing the polymer to solidify. The nozzles, core fluids, collection devices, and methods for varying the mechanical properties of the resulting fibers are similar to those used in air-gap spinning, as discussed further below.

Air-Gap Spinning

Hollow fiber asymmetric membranes can also be produced, for example, by air-gap spinning. In air-gap spinning, a polymer solution is extruded through a spinneret suitable for forming the hollow fiber. While the fiber is spinning, a gas or liquid may be injected into the bore of the hollow fiber extrudate to maintain the configuration of the hollow fiber. The resulting hollow fiber extrudate travels through an air-gap prior to coagulation by known techniques, for example contacting the extrudate with a non-solvent for the polymer. The fibers can then be collected onto a take-up roll or other suitable collection device.

The hollow fiber spinning process depends on many variables which may affect the morphology and properties of the hollow fiber membrane. These variables include the composition of the polymer solution employed to form the fiber, the composition of fluid injected into the bore of the hollow fiber extrudate during spinning, the coagulation medium employed to treat the hollow fiber extrudate, the rapidity of coagulation of the polymer, the rate of extrusion of the fiber, take-up speed of the fiber onto the take-up roll, and the like. The combination of the volumetric rate of supply, measured in terms of (cubic centimeters of dope/unit time), of the spin dope to the spinneret and the rate of fiber take up can be varied to control production rate, fiber size, morphology and draw ratio.

The nascent membrane can be passed through an air gap into a coagulation medium to coagulate the membrane into a sustainable structure. The resultant membrane can then be wound onto a take-up roll or other suitable collection device. The rate of extrusion of the polymer solution and the rate of take-up of the hollow membrane can be varied to optimize the mechanical and permeation properties of the hollow membranes.

The spinneret used to form the fiber membranes is generally of the tube-in-orifice type. Such spinnerets are well known in the art, as shown for example, in U.S. Pat. No. 4,127,625, the contents of which are hereby incorporated by reference. The spinnerets employed in the process of the invention are maintained during extrusion at a temperature sufficient to attain a viscosity of the spin dope sufficient to facilitate draw down of the nascent fiber. Generally, the spinneret may be maintained at 40 to 130° C., preferably 60 to 100° C.

While the fiber is spinning in the spinneret, a bore fluid is injected within the bore of the fiber to assist in maintaining the configuration of the fiber. The bore fluid can be a mixture of a solvent and a non-solvent for the polymer to permit a slow rate of coagulation and to permit draw down of the fiber, or it can be an inert gas such as $N_2$. Suitable bore fluids include, but are not limited to, water, N-methylpyrrolidone (NMP), dimethylformamide (DMF), and dimethylacetamide (DMAc). Preferably, the bore fluids include mixtures of solvents such as DMAc, NMP, DMF, and the like with water.

After the fibers exit the spinneret, the fibers are briefly exposed to an air gap of a gaseous atmosphere immediately before contacting a fluid coagulation bath. The choice of pressure, temperature, composition of the atmosphere, and the period of exposure of the fiber to the gaseous atmosphere are chosen to control the morphology of the nascent fiber.

Typically, the nascent fiber travels through the air-gap at room temperature. The temperature of the air gap can be varied to facilitate evaporation of the solvent from the nascent fiber. Generally, the air gap may be at ambient, as well as elevated temperatures. Preferably, the air gap is at ambient temperature.

The composition of the gaseous atmosphere of the air-gap is generally chosen to facilitate evaporation of the solvent from the fiber. Possible gas compositions include, but are not limited to; air, nitrogen, inert gases such as He, Ar, Xe and the like. Alternatively, reduced pressure may be employed in the air gap. Preferably, air is employed in the air gap.

After contacting the gaseous atmosphere of the air gap, the fibers are passed into a coagulation bath to coagulate the fiber prior to being wound onto a take-up roll. The choice of bath composition and temperature is made to control the rate of coagulation and morphology of the fiber. Possible compositions of the coagulation bath that may be employed in the invention include, but are not limited to water, aliphatic alcohols, mixtures of aliphatic alcohols, and mixtures of aliphatic alcohols with water. Other possible compositions for the coagulation bath include aqueous solutions of DMF, NMP, and DMAc. Preferably, the bath composition is water. The temperature of the coagulation bath can be varied to control the rate of coagulation and fiber morphology. After treatment of the fiber in the coagulation bath, the fibers are wound onto a take-up roll or other suitable collection device.

The speed of drawing of the fiber by devices such as continuous rolls and fluid jets, and the velocity of extrusion of the fiber are controlled to affect the draw ratio to provide improved permeation and mechanical properties in the resulting fiber membranes.

The ratio of the drawing speed of the fiber to the extrusion velocity of the fiber may be varied over wide limits. Generally, the rate of extrusion velocity of the fiber may vary from 2 to 100 meters/minute. Similarly, the rate of drawing of the fiber may vary from 1 to 500 meters/minute.

The resulting fiber membranes are preferably washed to remove residual solvent and the like, and then dried. Typically, washing is accomplished by placing the fiber membranes into water at 25 to 100° C., preferably 25 to 75° C. for a period sufficient to remove substantially all residual solvent as well as other impurities such as residual spin dope. Thereafter, the fibers are air dried or dehydrated by solvent exchange. For example, polyaramide can be two step solvent exchange dehydrated by first using methanol and then hexane. Such methods of solvent exchange dehydration are known in the art, as described in U.S. Pat. Nos. 4,080,743; 4,080,744; and 4,120,098, which are incorporated by reference herein. Alternatively, the fibers may be dehydrated by heating in an atmosphere such as air, and the like.

The resulting hollow fibers typically have an outside diameter of about 75 to 700 microns, desirably 100 to 300 microns. Preferably, the diameter of the bore of the fiber is 30 to 60 percent of the outside diameter of the fiber.

Three-way co-extrusion can be used to form the membranes. In this type of method, gas or liquid is extruded through the center to form a void. A polymer, preferably a porous polymer, is used as a support, and is extruded next to and around the gas or liquid. The polymer/zeolite mixture is added next to and around the support layer, forming an asymmetric hollow fiber. Alternatively, the polymer/zeolite can be next to and around the gas/liquid, and the polymer support layer can be extruded on next to and around the polymer/zeolite layer. An example of such an asymmetric hollow fiber is shown in FIG. 1. FIG. 1 is a cross section of the hollow fiber, showing a void (10), a relatively thick polymer layer (20) and a relatively thin polymer/zeolite layer (30). The zeolite particles (40) are encapsulated by the polymer matrix (50).

Methods of Using Hollow Fibers

Hollow fibers can be employed in bundled arrays potted at either end to form tube sheets and fitted into a pressure vessel thereby isolating the insides of the tubes from the outsides of the tubes. Devices of this type are known in the art.

Preferably, the direction of flow in a hollow fiber element will be counter-current rather than co-current or even transverse. Such counter-current flow can be achieved by wrapping the hollow fiber bundle in a spiral wrap of flow-impeding material. This spiral wrap extends from a central mandrel at the center of the bundle and spirals outward to the outer periphery of the bundle. The spiral wrap contains holes along the top and bottom ends whereby fluid entering the bundle for tube side flow at one end is partitioned by passage through the holes and forced to flow parallel to the hollow fiber down the channel created by the spiral wrap. This flow direction is counter-current to the direction of flow inside the hollow fiber. At the bottom of the channels the fluid re-emerges from the hollow fiber bundle through the holes at the opposite end of the spiral wrap and is directed out of the module.

Xylene Purification Process

A mixture containing p-xylene and m-xylene can be enriched in p-xylene by a gas-phase, perstraction or pervaporation process through the composite membrane, for example in any of the above-configurations. Superior results are obtained when pervaporation conditions are used.

Perstraction involves the selective dissolution of particular components contained in a mixture into the membrane, the diffusion of those components through the membrane and the removal of the diffused components from the downstream side of the membrane by using a liquid sweep stream.

The xylenes present in the feedstream dissolve into the membrane film due to similarities between the membrane solubility parameter and those of the xylenes. The xylenes then permeate (diffuse) through the membrane, with p-xylene permeating at a significantly higher rate than m-xylene, and are swept away by a sweep liquid that is low in xylene content. This keeps the concentration of xylenes at the permeate side of the membrane film low and maintains the concentration gradient which is responsible for the permeation of the xylenes through the membrane.

The sweep liquid is low in xylene content so as not to itself decrease the concentration gradient. The sweep liquid is preferably a saturated hydrocarbon liquid with a boiling point much lower or much higher than that of the permeated xylenes. This facilitates separation, for example by simple distillation. Suitable sweep liquids include, for example, $C_3$ to $C_6$ saturated hydrocarbons and lube base stocks ($C_{15}$–$C_{20}$). If $C_3$ or $C_4$ sweep liquids are used at 25° C. or above in liquid state, the pressure must be increased to keep them in the liquid phase.

The perstraction process is run at any convenient temperature, preferably as low as practical.

The choice of pressure is not critical since the perstraction process is not dependent on pressure, but on the ability of the xylenes in the feed to dissolve into and migrate through the membrane under a concentration driving force. Consequently, any convenient pressure may be employed, the lower the better to avoid undesirable compaction, if the membrane is supported on a porous backing, or rupture of the membrane, if it is not.

Pervaporation, with the feed liquid phase or gas phase separation, is run at generally higher temperatures than perstraction with the feed in either liquid or vapor form. Pervaporation relies on vacuum or a sweep gas on the permeate side to evaporate or otherwise remove the permeate from the surface of the membrane and maintain the concentration gradient driving force which drives the separation process. As in perstraction, the xylenes present in the feed dissolve into the membrane film, migrate through the film and reemerge on the permeate side under the influence of a concentration gradient. Pervaporative separation can be performed at a temperature of about 25° C., but is preferably performed at temperatures of at least 80° C., preferably at least 100° C., and more preferably, 120° C. and higher (typically up to about 170 to 200° C.). The maximum upper limit is typically the temperature at which the membrane is physically damaged. Vacuum on the order of 1–50 mm Hg is pulled on the permeate side. The vacuum stream containing the permeate is cooled to condense out the permeate. Condensation temperature should be below the boiling point of the permeate at a given vacuum level.

The membrane itself may be in any convenient form using any convenient module design. Sheets of the composite membrane may be used in spiral wound or plate and frame permeation cell modules. Tubes and hollow fibers of the composite membranes may be used in bundled configurations with either the feed or the sweep liquid (or vacuum) in the internal space of the tube or fiber, and the feed stream on the other side.

For perstraction, the membrane is preferably used in a hollow fiber configuration with the feed introduced on the exterior side of the fiber and the sweep liquid flowing on the inside of the hollow fiber. The sweep fluid sweeps away the permeated xylenes, and maintains the desired concentration gradient. The sweep liquid, along with permeate contained therein, can be passed to a separation means, typically a distillation means, or, alternatively, if the sweep liquid is volatile enough, it can simply be allowed to evaporate. The sweep liquid can then be recovered and re-liquefied under pressure and/or by lowering the temperature.

Preferred conditions for enriching by perstraction are any combination of feed pressure and temperature where the temperature is just below the boiling point at that pressure. Permeate pressures should be below the feed pressure enough to ensure complete vaporization at the operating temperature. Preferable ranges are temperatures between 30 and 150° C., and feed pressures of 14 psia to 35 psia. Permeate pressures have a preferred range of 0 to 190 inches of vacuum gauge. These conditions can be varied if components from other feed streams, for example those including ethylbenzene or alkylated napthalenes, are to be purified and isolated.

In addition to purifying p-xylene and m-xylene, as well as o-xylene and ethylbenzene, the membranes can be used to separate any gases which are known to be separated using zeolites, by selecting the appropriate zeolite to incorporate into the polymer membrane.

Additional Purification

If additional purification is required, the product in the permeate stream can be passed through additional membranes, and/or the product can be crystallized using techniques well known to those of skill in the art.

Membrane Evaluation

The composite membranes can be evaluated using routine experimentation. For example, a mixture including p-xylene and m-xylene can be passed through one or more polymer membranes, and the enrichment of the permeate stream in p-xylene analyzed, for example, using gas chromatography. Those membranes which provide a useful enrichment (at least about 10% by weight enrichment) are within the scope of the invention described herein.

The present invention will be better understood with reference to the following non-limiting examples.

EXAMPLE 1

Dense Film Preparation for PX Separation Testing

Materials

SPO is a polyaramide synthesized from m-phenylene diamine and 70:30 isophthalic: terephthalic acids. SPO was dissolved in dimethyl acetamide (DMAc) to form a 25% (w/w) solution I.

Cellulose acetate (CA) (39.7% acetyl content) was dried in a vacuum oven at 120° C. and dissolved in dioxane to form a 20% (w/w) solution II.

Zeolite (either Silicalite or ZSM-5) is commercially available and was dried at 120° C. and stored in a desiccator.

SP-0 MMC Dense Films 0.74 g of zeolite was dispersed in 4.3 g of DMAc and dispersed with ultrasonication. The suspension was mixed with 14.6 g of solution I and further dispersed by ultrasonication. A film was cast from this solution using a knife set at 0.75 mm on a glass plate heated to 55° C. The film was removed after 12–16 hours and then hung with a small load in a vacuum oven (180–200° C.) for 10–14 days. The dried film is estimated to have a zeolite/SP-0 weight ratio of 0.2.

CA MMC Dense Films 0.52 g of zeolite was dispersed in 5.9 g of dioxane and dispersed with ultrasonication. The suspension was mixed with 12.9 g of solution II and further dispersed by ultrasonication. A film was cast from this solution using a knife set of 0.75 mm on a glass plate at ambient temperature. The film was removed after 12–16 hours and then dried in a vacuum oven (120° C.) for 7–10 days. The dried film is estimated to have a zeolite/CA weight ratio of 0.2.

EXAMPLE 2

Xylenes Separation Testing

As discussed below, various membranes were prepared and evaluated for their ability to separate p-xylene from a 1:1 mixture of p-xylene and m-xylene. Certain of the membranes were able to separate p-xylene from m-xylene with high selectivity, whereas others were unable to separate p-xylene from m-xylene.

A) SPO-silicalite

A composite membrane was cast from a dimethyl acetate (DMAc) solution of SPO polymer (as described above in Example 1) which had a silicalite: SPO weight ratio of 0.20. The membrane was tested under two test conditions, a 45° C. pervaporation mode and a 150° C. vapor phase mode. The selectivity (p-xylene/m-xylene) for the pervaporation mode was 6, and the selectivity for the vapor phase mode was 1.2.

A similar membrane was cast from a dioxane solution of CA, and exhibited a selectivity of about 1.

B) CA-ZSM-5

Figure 2:
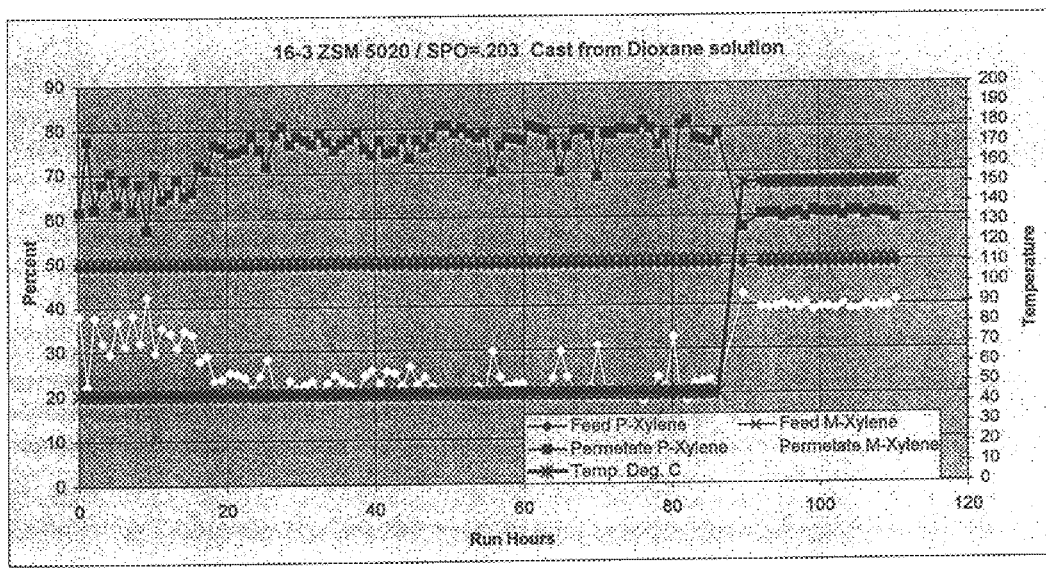
FIG. 2 is a graph showing the percentages of p-xylene and m-xylene in the feedstream and permeate for a SPO polymer membrane including ZSM-5 particles, as described in Examples 1 and 2.

A composite membrane was cast from a dioxane solution of CA polymer (as described above in Example 1) which included about 20.3 wt. percent ZSM-5, which had a SiO2/Al2O3 molar ratio of 50. The membrane was tested under two test conditions, a 45° C. pervaporation mode and a 150° C. vapor phase mode. The selectivity (p-xylene/m-xylene) for the pervaporation mode was 4, and the selectivity for the vapor phase mode was 2. The results are shown in FIG. 2. As shown in FIG. 2, pervaporation is preferred over vapor phase for this membrane.

A similar membrane was cast from a DMAc solution of SPO, and exhibited a selectivity of about 1.

EXAMPLE 2

Diffusivity of Para-xylene in a Mixed Matrix Membrane

Figure 3:
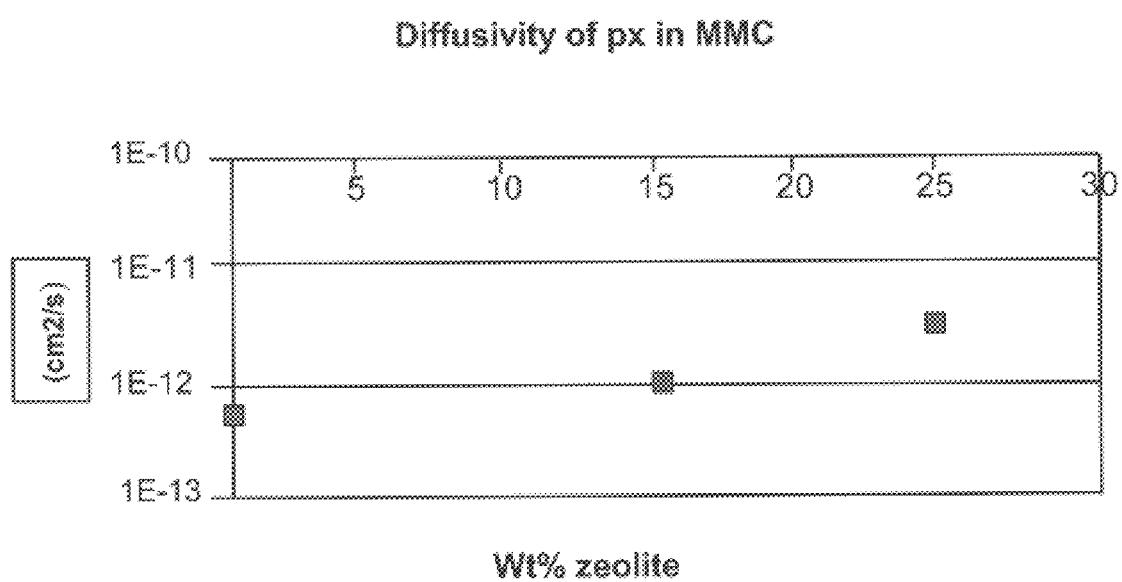
FIG. 3 is a graph showing the diffusivity ($cm^2/s$) of p-xylene versus the wt. % zeolite in a mixed membrane composite including zeolite particles and an SPO polymer.

Three mixed matrix membranes including an SPO polymer and differing levels of ZSM-5 (0, 15 and 25% by weight) were prepared. The rates of permeation of p-xylene through the membranes were measured. The apparent membrane diffusivities were then calculated using the measured fluxes, membrane thickness, and using the driving force equal to the vapor pressure of a xylene feed. This latter value is calculated using the vapor pressure of p-xylene over a 50% solution at 45° C. (i.e., yi phi P=xi gamma Psat) and an assumed ideal gas solution. The results are shown in FIG. 3. As shown in FIG. 3, the effective diffusivity increases with increased zeolite loading (assuming that the diffusivity through the polymer is lower than through a pure zeolite).

The partial pressure of permeate xylene was assumed to be equal to zero, since a large sweep gas flowrate was used.

What is claimed is:

1. A process for removing p-xylene from a feedstream including p-xylene and m-xylene, the process comprising:
   a) providing a polymer membrane comprising non-interconnected zeolite particles having feed and permeate sides and that is selectively permeable to p-xylene over m-xylene, and
   b) directing a feedstream including p-xylene and m-xylene to the feed side of the membrane and withdrawing a retentate stream depleted in p-xylene and withdrawing a permeate stream enriched in p-xylene from the permeate side of the membrane;

wherein the permeability of p-xylene through the zeolite is greater than the permeability of p-xylene through the polymer.

2. The process of claim 1, wherein the membrane is in the form of a film or a hollow fiber.

3. The process of claim 1, wherein the polymer is selected from the group consisting of cellulose polymers, polyaramides, polyamides, polyimides, polyamide/imides, polyamidehydrazides, polyhydrazides, polyimidazoles, polybenzoxazoles, polyvinylidene fluorides, polyester/amide, polyester/imide, polycarbonate/amides, polycarbonate/imides, polysulfone/amides, polysulfone imides, and copolymers and blends thereof.

4. The process of claim 1, wherein the polymer is a polyaramide or cellulose polymer.

5. The process of claim 1, wherein the zeolites are intermediate pore size zeolites.

6. The process of claim 1, wherein the zeolite is an MFI zeolite.

7. The process of claim 1, wherein the thickness of the membrane is between 10 and 1000 microns.

8. The process of claim 1, wherein the weight ratio of zeolite to polymer is between about 0.05 and 0.4.

9. The process of claim 1, wherein the polymer membrane comprises a relatively thin layer between 0.1 and 3.0 microns in thickness comprising the polymer and zeolite, and a relatively thick layer comprising the polymer, wherein the thickness of the two layers is between about 10 and 1000 microns.

10. The method of claim 1, wherein the zeolite particles are silanated.

11. The method of claim 10, wherein the silanation is performed by contacting zeolite particles with a suitable silane for at least one minute, and recovering the silanated zeolite particles.

12. The process of claim 1, wherein the feedstream comprises the product stream from a reforming reaction.

13. The process of claim 12, wherein the reforming reaction comprises reforming a hydrocarbon feed having a sulfur concentration of below 100 ppb over a catalyst comprising a type L zeolite containing at least one Group VIII metal to produce aromatics and hydrogen.

14. The process of claim 12, wherein the reforming reaction is a platforming or rheniforming process.

15. A composite membrane comprising:
   a) a polymer selected from the group consisting of cellulose polymers, polyaramides, polyamides, polyimides, polyamide/imides, polyamidehydrazides, polyhydrazides, polyimidazoles, polybenzoxazoles, polyvinylidene fluorides, polyester/amide, polyester/imide, polycarbonate/amides, polycarbonate/imides, polysulfone/amides, polysulfone imides, and copolymers and blends thereof; and
   b) non-interconnected zeolite particles disposed in the polymer;

wherein the membrane is in the form of a film or a hollow fiber.

16. The membrane of claim 15, wherein the thickness of the membrane is between 10 and 1000 microns.

17. The membrane of claim 15, wherein the polymer membrane comprises a relatively thin layer between 0.1 and 3.0 microns in thickness comprising the polymer and zeolite, and a relatively thick layer comprising the polymer, wherein the thickness of the two layers is between about 10 and 1000 microns.

18. The membrane of claim 15, wherein the weight ratio of polymer to zeolite is between about 0.05 and 0.4.

19. The membrane of claim 15, wherein the polymer is a polyaramide.

20. The membrane of claim 15, wherein the polymer is a polyaramide or cellulose polymer.

21. The membrane of claim 15, wherein the zeolites are intermediate pore size zeolites.

22. The membrane of claim 15, wherein the zeolite is an MFI zeolite.

23. A method for forming a composite membrane comprising:
   a) extruding gas or liquid to form a void,
   b) extruding a relatively thick layer of a polymer next to and around the gas or liquid to form a polymer support layer, and
   c) extruding a relatively thin layer of a polymer/zeolite next to and around the polymer support layer.

* * * * *